US010875059B2

(12) United States Patent
Bauer

(10) Patent No.: US 10,875,059 B2
(45) Date of Patent: Dec. 29, 2020

(54) METHOD AND APPARATUS FOR AUTOMATED PARTICULATE EXTRACTION FROM SOLID PARTS

(71) Applicant: Automatic Spring Products Corp., Grand Haven, MI (US)

(72) Inventor: Nathaniel David Bauer, Grand Haven, MI (US)

(*) Notice: Subject to any disclaimer, the term of this patent is extended or adjusted under 35 U.S.C. 154(b) by 15 days.

(21) Appl. No.: 16/194,643

(22) Filed: Nov. 19, 2018

(65) Prior Publication Data

US 2019/0151904 A1 May 23, 2019

Related U.S. Application Data

(60) Provisional application No. 62/589,253, filed on Nov. 21, 2017.

(51) Int. Cl.
  *B08B 3/04* (2006.01)
  *B08B 3/10* (2006.01)
  (Continued)

(52) U.S. Cl.
  CPC ............. *B08B 3/04* (2013.01); *B08B 3/102* (2013.01); *B08B 3/12* (2013.01); *A47L 15/4244* (2013.01);
  (Continued)

(58) Field of Classification Search
  CPC .. A47L 15/13; A47L 15/4297; A47L 15/4244; A47L 2601/17; A47L 2401/10; A47L 2401/09; A47L 2401/14; A47L 15/00; A47L 15/0039; A47L 15/0049; A47L 15/4202; A47L 15/4204; A47L 15/4206; A47L 15/4208; A47L 15/0018; A47L 15/0031; A47L 15/0028;
  (Continued)

(56) References Cited

U.S. PATENT DOCUMENTS 4,731,154 A 3/1988 Hausman Hazlitt
4,826,538 A 5/1989 Sanders
(Continued)

OTHER PUBLICATIONS

American Water Works Association, Microfiltration and Ultrafiltration Membranes for Drinking Water, 66 (2d ed. 2016). (Year: 2016).*

*Primary Examiner* — Mikhail Kornakov
*Assistant Examiner* — Richard Z. Zhang
(74) *Attorney, Agent, or Firm* — Hultman Law, PLC; Eric Andrew Hultman Esq.

(57) ABSTRACT

A method and apparatus for automated particulate extraction from solid parts is disclosed herein, which comprises a test tank (42) and a liquid cleaning medium (46) for washing a test part (48). The principle advantages offered by this invention include the ability to verify that the test tank (42) has met a required tank clean threshold (102) as specified by a percentage reduction of contaminants (78) through the use of a liquid quality sensor (76) which repeatedly measures the contamination level of a liquid cleaning medium (46) exiting the test tank (42). Type I and Type II sampling error are eliminated by verifying that the liquid cleaning medium (46) passing from the test tank (42) has measured contaminants (78) reaching both a maximum value (98) and then falling below a specified tank clean threshold (102) prior to ending the cleaning cycle.

24 Claims, 8 Drawing Sheets

(51) Int. Cl.
*B08B 3/12* (2006.01)
*F16K 11/074* (2006.01)
*A47L 15/42* (2006.01)
*A47L 15/46* (2006.01)
*G01F 1/00* (2006.01)

(52) U.S. Cl.
CPC ........... *A47L 15/46* (2013.01); *A47L 2401/14* (2013.01); *F16K 11/074* (2013.01); *G01F 1/007* (2013.01)

(58) Field of Classification Search
CPC .. A47L 15/46; B08B 3/04; B08B 3/12; B08B 9/08; B08B 9/093; B08B 9/0813; B08B 9/46; B08B 3/00; B08B 9/00; B08B 3/102; D06F 39/003; D06F 39/004; D06F 2202/10; D06F 39/00; D06F 33/00; D06F 39/10; D06F 39/082; D06F 32/002; C23G 1/36; C23G 3/00
See application file for complete search history.

(56) References Cited

U.S. PATENT DOCUMENTS

| | | | |
|---|---|---|---|
| 5,331,177 A * | 7/1994 | Kubisiak | A47L 15/4297 250/574 |
| 5,385,159 A * | 1/1995 | Mead | B08B 3/006 134/104.4 |
| 5,800,628 A | 9/1998 | Erickson | |
| 5,922,606 A | 7/1999 | Jenkins | |
| 5,931,173 A | 8/1999 | Schiele | |
| 6,203,659 B1 | 3/2001 | Shen | |
| 6,238,487 B1 | 5/2001 | Jenkins | |
| 6,328,828 B1 | 12/2001 | Rusczyk | |
| 6,347,636 B1 | 2/2002 | Xia | |
| 6,379,538 B1 | 4/2002 | Corlett | |
| 6,482,325 B1 | 11/2002 | Corlett | |
| 6,488,037 B1 | 12/2002 | Guldi | |
| 6,544,344 B2 | 4/2003 | Hegeman | |
| 6,605,157 B2 | 8/2003 | Hegeman | |
| 6,615,853 B2 | 9/2003 | Hegeman | |
| 6,622,754 B1 | 9/2003 | Roth | |
| 6,641,058 B2 | 11/2003 | Hegeman | |
| 6,698,438 B2 | 3/2004 | Hegeman | |
| 6,752,875 B2 | 6/2004 | Kiesler | |
| 6,832,617 B2 | 12/2004 | Hegeman | |
| 6,868,700 B2 | 3/2005 | Sawa | |
| 7,163,589 B2 | 1/2007 | Kaiser | |
| 7,534,304 B2 | 5/2009 | Conrad | |
| 7,803,231 B2 | 9/2010 | Katano | |
| 7,874,306 B2 | 1/2011 | Wu | |
| 7,981,286 B2 | 1/2011 | Higuchi | |
| 8,002,903 B1 | 8/2011 | Tarr | |
| 8,092,614 B2 | 1/2012 | Doherty | |
| 8,132,279 B1 | 3/2012 | Tarr | |
| 8,161,995 B2 | 4/2012 | Armstrong | |
| 8,221,554 B2 | 7/2012 | Thiyagarajan | |
| 8,404,056 B1 | 3/2013 | Chen | |
| 8,441,646 B2 * | 5/2013 | Fauth | D06F 34/22 356/442 |
| 8,470,137 B2 | 6/2013 | Publ | |
| 8,506,761 B2 | 8/2013 | Publ | |
| 8,522,810 B2 | 9/2013 | Armstrong | |
| 8,540,820 B2 | 9/2013 | Allen | |
| 8,545,636 B2 | 10/2013 | Miller | |
| 8,603,255 B2 | 12/2013 | Classen | |
| 8,834,646 B2 | 9/2014 | Bewley | |
| 8,863,763 B1 | 10/2014 | Chen | |
| 8,888,931 B2 | 11/2014 | Watson | |
| 8,968,486 B2 | 3/2015 | Allen | |
| 8,992,691 B2 | 3/2015 | Henry | |
| 8,992,694 B2 | 3/2015 | Gnadinger | |
| 9,005,369 B2 | 4/2015 | Delgado | |
| 9,027,578 B2 | 5/2015 | Boyer | |
| 2002/0137650 A1* | 9/2002 | Okumura | B01D 65/02 510/247 |
| 2003/0019510 A1* | 1/2003 | Hegeman | A47L 15/0049 134/18 |
| 2003/0102007 A1 | 6/2003 | Kaiser | |
| 2005/0028850 A1* | 2/2005 | Nito | A47L 15/0049 134/200 |
| 2005/0092352 A1 | 5/2005 | Luckman | |
| 2009/0120474 A1* | 5/2009 | Kehl | A47L 15/0002 134/58 D |
| 2010/0064445 A1* | 3/2010 | Nieh | D06F 35/006 8/159 |
| 2012/0048300 A1* | 3/2012 | Thiyagarajan | A47L 15/4202 134/10 |

* cited by examiner

METHOD AND APPARATUS FOR AUTOMATED PARTICULATE EXTRACTION FROM SOLID PARTS

CROSS REFERENCE TO RELATED APPLICATION

This application is a non-provisional application claiming priority to an earlier filed U.S. provisional patent application entitled, "Method and apparatus for automated particulate extraction from solid parts," filed Nov. 21, 2017, and assigned Ser. No. 62/589,253, the contents of which are incorporated herein by reference.

BACKGROUND OF THE INVENTION

Field of the Invention

The present invention generally relates to processes for extracting non-dissolved particulates from solid parts, more specifically to processes for extracting non-dissolved particulates from solid parts using a liquid cleaning medium, and particularly to processes for extracting non-dissolved particulate from solid parts using a liquid cleaning medium, wherein the cleaning process is controlled via the monitoring of contaminant levels present in the liquid cleaning medium via an in-line liquid quality sensor.

Description of the Related Art

In today's manufacturing environment, contaminants are ever present as a product of the manufacturing process. As the manufacturing environment requires ever tighter control on contaminants, there is a demand to ensure that parts supplied for critical assemblies meet or exceed a minimum cleanliness criterion. In the specific case of parts installed inside liquid lubricated machines, these parts must be supplied without contaminants which would be determinantal to the function of the machine. For these parts, there exists both a maximum allowable non-dissolved particulate size and a numerical threshold above which the total count of smaller foreign body particulates become so numerous that they become detrimental to the machine's function. Therefore, testing exists wherein the largest particulate matter is measured alongside an estimate of the overall particulate count of non-dissolved solids on the part. Parts are tested, and then compared to a specified threshold to determine if a supplied part has met the required level of cleanliness to be used safely within the machine.

Traditional testing for non-dissolved particulate contamination involves first validating the test machine's capability. A sample part is washed according to a predetermined method which typically involves hand spraying a liquid cleaning medium of a known volume at a known pressure at the test part. The particulate matter dislodged by the cleaning fluid is then collected via a filter medium which is later analyzed to determine a base level of part contamination. The machine is then reset, the filters replaced, and the process is then repeated using the same part. The filter contamination from the second test is then compared against the filter contamination from the first test to determine the overall percentage of reduction in particulate matter. The cleaning machine's process is deemed capable when the filters from the second cleaning indicate that a predetermined percentage of contaminant reduction between the two tests was met by the second test.

However, once the machine is validated as capable, henceforth the machine is utilized for contaminant testing using only a single contamination test per part. During this single test, a test part is washed, and the filter reviewed to determine if the contamination on the filter is below a certain level of contamination. This provides two types of error, a Type I, false positive, where the cleaning process failed, so the filter is negligibly contaminated—indicating that the part is clean when in fact the cleanliness is unknown or not acceptable. The other type of error is a Type II error, a false negative, wherein the test machinery itself is contaminated, but the parts are clean. Here, the residual contaminants within the test apparatus from a prior wash cycle moves onto the filter indicating a condition where contamination level exceed the acceptability criteria and an otherwise acceptable part is deemed to have failed the test.

Most concerning, and a current issue in testing facilities, is that the test criteria for contamination, e.g. the acceptable criteria for non-dissolved solid contaminants, is largely based on the surface area of the part being tested. Thus, a part with a large surface area may contain a higher total count of contaminants and still pass. If a large part such as a transmission housing is tested in the measurement apparatus just prior to a small surface area part, such as a spring, the residual contamination remaining in the test tank from the processing of the larger part may cause the smaller part's test to fail, when in reality the test is experiencing a Type II error due to the test tank being contaminated at the start of the smaller part's test. Worse yet, the contamination levels within the tank itself is not tracked and tends to accumulate with repeated testing.

The accumulating contamination problem is diagrammed in FIG. 1—Prior Art, at 20 generally wherein the test chamber's contamination level is graphed against time for two consecutive cleaning cycles. The contamination level in the machine is initially zero 22 at the beginning of the first test. As the test proceeds, contaminants become dislodged from the part and build up in the text tank reaching a maximum point at 24. The traditional part cleaning cycle 25 then continues until completion according to when either a fixed time has elapsed, or volumetric based test criteria are met. The part is then removed from the chamber and the filters are removed for further testing. This leaves a residual amount of contamination in the test chamber as shown at point 26. The second cycle then begins, contaminants are washed off the second part contaminating the chamber and reaching a maximum at point 28. However, in addition to cleaning the part, some but not all, of the contaminants left in the test tank 29 from the first test are also removed and accumulate in the filter. This additional increase in particulates is shown at 30, and the portion of extra contaminants remaining in the chamber after tests one and two are shown at 32. Thus, at the beginning of test three, there is an accumulation of contaminants 29 which is some combination of the previous tests, and the filter medium used to analyze the contaminants from the third test may indicate a Type II error (false negative) due to the extra residual contamination (26, 32) present in the chamber from the preceding tests.

Prior art solutions to this problem have required an 'occasional' manual flush of the machine prior to testing, but the machines themselves are not verified to be clean prior to the next sample being processed. This manual flush of the test chamber is largely left up to the discretion of the operator, and the flushing is typically done for a fixed duration based via a cycle timer with no feedback on machine's actual cleanliness. Moreover, even if the machine were re-validated for capability, the capability test itself would not confirm if the machine is clean. The capability test merely confirms that the difference between any two tests can meet a required reduction in particulates, and since the contamination test uses a pass/fail criterion based on measured contaminants for a given part's surface area, the test is largely dependent on the surface area of the parts placed into the machine, rather than the base cleanliness of the machine itself. To verify that the machine is clean using traditional methods would require that a blank test cycle be run a second time, using an empty tank. This of course ties up the machine for an additional cycle and is inefficient. This blank test further is a pass/fail test and can tell you if the machine is clean, but cannot identify when during the last cleaning cycle this status occurred. Thus, the machine is tied up for a longer period of time than is needed to achieve the cleanliness target.

Another solution contains instructions to run part cleaning cycles using increasing time intervals. This provides a set of datapoints which when aggregated can determine the approximate timing for when a particular part may pass the cleanliness test. These discrete test points can be used to extrapolate an approximate contamination versus cleaning time curve for a specific part being tested. Again, this is merely educated guessing, and assumes that the existing trends and similar historical data doesn't vary (and due to accumulated debris in the test tank, we know that it does). This type of curve is considered to be 'fixed', and is not adjusted once established for the part.

Using this fixed approximate contamination curve on subsequent runs, the machine may be set to run the machine for a proscribed amount of time based on the derived cleanliness curve for that part. However, if any baseline information changes, such as a different part being run before, or during the test—the test will be unacceptably prone to a Type I error, wherein the cleaning process will vary from the predicted curve and go unnoticed. This will allow for otherwise unacceptably dirty parts to be passed. For additional information see testing information from test reference ISO-16232 (Rev. 2007) which is herein incorporated by reference.

A better approach to testing is needed. Our inventive process and apparatus automate the particulate extraction process by adding an analytic feedback system which measures the cleaning medium during the cleaning process, preferably with an inline liquid quality sensor. This feedback system monitors the testing process to both validate that the parts have reached the required level of cleanliness (preventing Type I error), while also allowing for verification that the test equipment is clean prior to allowing a second test to begin (preventing a Type II error).

This system may be further combined with a removable measurement filter medium in order to provide a traditional verification that the required testing parameters for a percentage of contaminant reduction are met. However, unlike traditional testing, and since additional tank cleaning is involved in the inventive process, a removable measurement filter bypass is included. The inventive removable measurement filter bypass prevents Type II error by bypassing the measurement filters once the proscribed level of contamination removal is measured according to the test standards.

SUMMARY OF THE INVENTION

In a first embodiment, we present a method for particulate extraction from solid parts is provided which comprises the steps of providing a test tank having at least one wall and a bottom portion, a liquid cleaning medium dispensing system, a liquid cleaning medium, a liquid quality sensor, and a drain line which allows the liquid cleaning medium to be removed from the test tank. A tank clean threshold is provided and test parts are placed into the test tank. The test part is then cleaned by allowing the liquid cleaning medium to contact both the test part and the test tank. This contaminates the liquid cleaning medium with a contaminant from either the part or the test tank. The contaminated liquid cleaning medium is then allowed to exit the test tank, wherein it is repeatedly measured for the amount of a contaminant present in the contaminated cleaning medium. This measurement is done with the liquid quality sensor, and is done repeatedly. To make sure the process operates as intended, the system verifies that the measured amount of the contaminant in the liquid initially increases and at a later point begins to decreases. The cleaning process continues until the measured amount of a contaminant in the liquid exiting the tank falls below the specified tank clean threshold wherein the cleaning step is stopped.

In a second embodiment, we present a method for particulate extraction from solid parts is provided which comprises the steps of providing a test tank having at least one wall and a bottom portion, a liquid cleaning medium dispensing system, a liquid cleaning medium, an inlet valve controlling the flow of the liquid cleaning medium into the liquid cleaning medium dispensing system, an inlet flow sensor, a liquid quality sensor, a processor having a memory, a scrubbing element which acts upon the liquid cleaning medium, an outlet valve, a drain line which allows the liquid cleaning medium to be removed from the test tank, a removable measurement filter downstream from the liquid quality sensor, and a bypass path around the removable measurement filter, the bypass path activated by a bypass valve. The system operates by storing at least one scrub parameter into the processor's memory. Liquid cleaning medium is sent past the liquid quality sensor where the liquid cleaning medium is measured, creating a baseline reading prior to cleaning the test part. This baseline reading is then stored into the processor's memory. A tank clean threshold is then calculated by multiplying a numerical percentage of desired tank cleaning by the baseline reading. This tank clean threshold is then stored into the memory. A test part is placed into the test tank. The amount of liquid cleaning medium entering the test tank is then measured with the flow meter while the test tank is then filled with liquid cleaning medium. Next, the test part is cleaned by operating the scrubbing element according to a provided scrub parameter, after which the test tank is then drained. The test part is then cleaned by allowing additional liquid cleaning medium to contact the test part and the test tank, thereby creating a contaminated liquid cleaning medium. This contaminated liquid cleaning medium is comprised of liquid cleaning medium which is contaminated by a contaminant dislodged from either the part, or from the test tank itself. This contaminated liquid cleaning medium is then allowed to exit the test tank, wherein the flow of the contaminated liquid cleaning medium exiting the test tank is controlled by operating the outlet valve. The contaminated liquid medium exiting the tank is then repeatedly measured with the liquid quality sensor to determine the amount of a contaminant present in the contaminated liquid cleaning medium. The processor is then used to determine that the measured amount of the contaminant initially increases from the baseline reading, achieves a maximum value, and then decreases from the maximum value. The maximum value of a contaminant as measured by the liquid quality sensor is then stored into the processor's memory. A part measurement threshold is then calculated by multiplying the numerical cleaning cutoff value by the maximum value of a contaminant. This part measurement threshold is also stored into the memory. After passing the liquid quality sensor, the contaminant present in the contaminated liquid cleaning medium is captured in the removable measurement filter. The processor continues to measure the data from the liquid quality sensor and when the measured amount of a contaminant falls below the part measurement threshold, the bypass valve is activated bypassing the flow of contaminated liquid cleaning medium around the removable measurement filter. The liquid cleaning medium then continues to supply liquid cleaning medium to the dispensing system and the outflow of contaminated liquid cleaning medium exiting from the tank is measured by the liquid quality sensor. This continues until the measured amount of a contaminant falls below the tank clean threshold, wherein the flow of liquid cleaning medium is stopped. The removable measurement filter is then removed, possibly for additional testing. The part is then removed from the test tank completing the process.

BRIEF DESCRIPTION OF THE DRAWING FIGURES

Other advantages of the present invention will be readily understood by reference to the following detailed description in connection with the accompanying drawings wherein.

DESCRIPTION OF THE VARIOUS EMBODIMENTS

Figure 1:
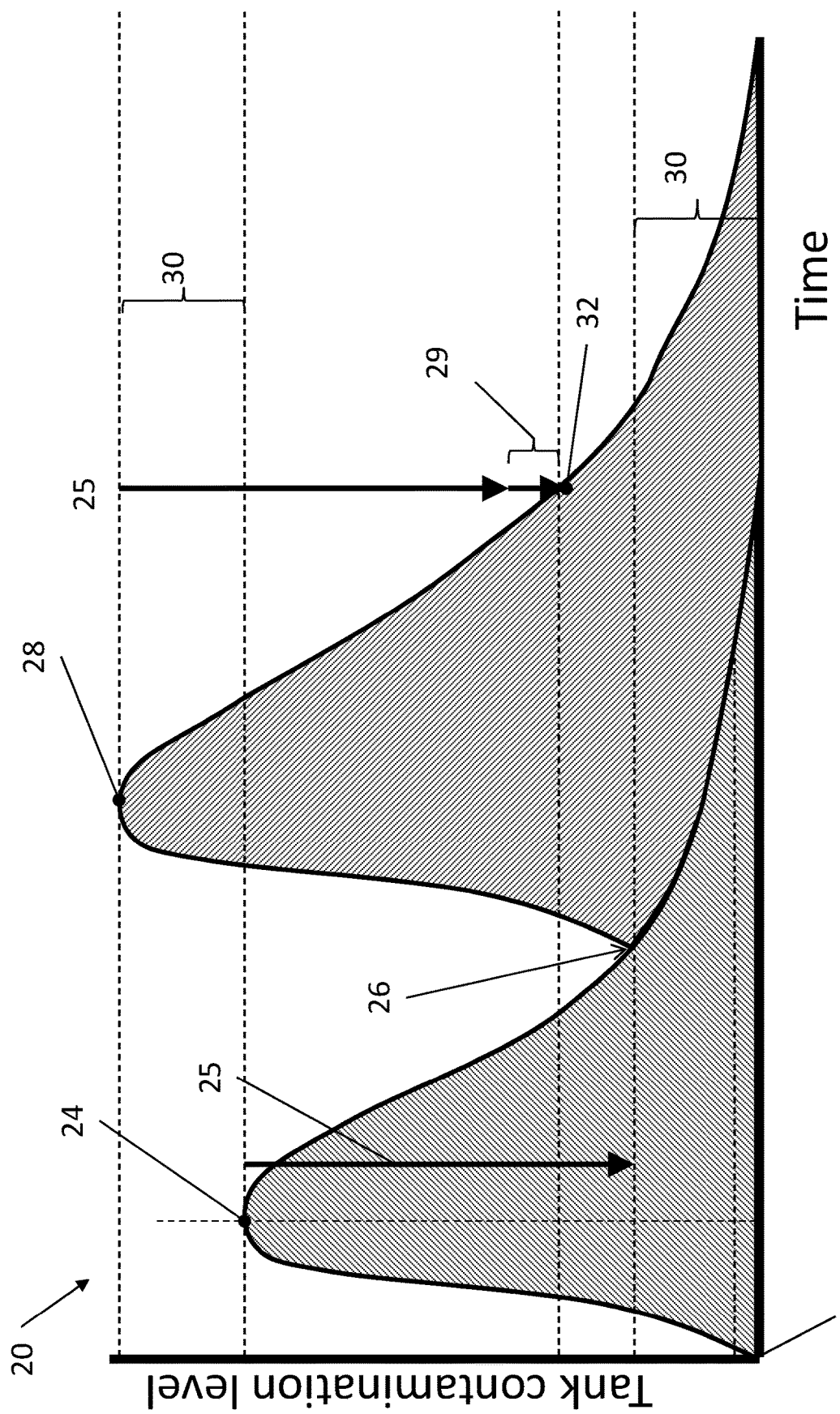
FIG. 1 is graph showing theoretical contamination buildup over time in a test chamber using a conventional (prior-art) testing process.
Figure 2:
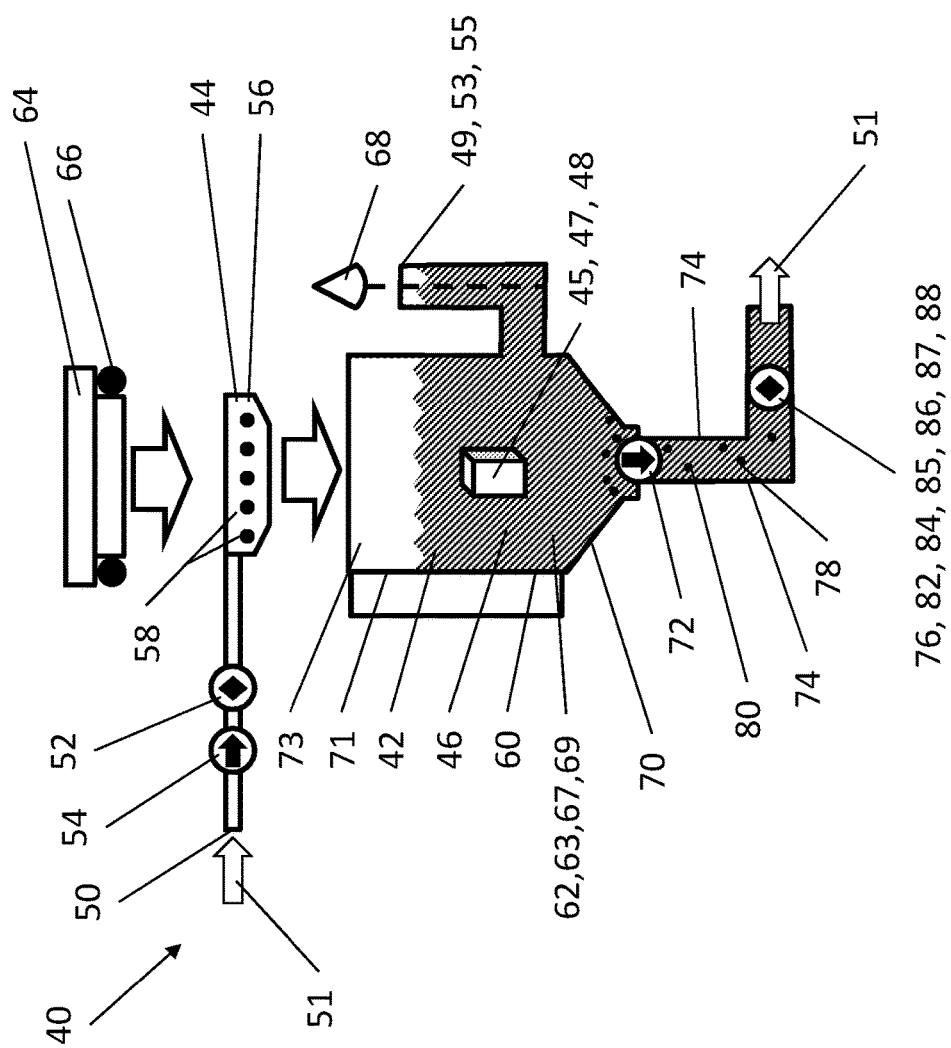
FIG. 2 is an elevation view of an apparatus according to a first form of the invention.

For purposes of the following description, the terms "upper," "lower," "left," "rear," "front," "vertical," "horizontal" and derivatives of such terms shall relate to the invention as oriented in FIG. 2. However, it is to be understood that the invention may assume various alternative orientations and configuration, except where expressly specified to the contrary. It is also to be understood that the apparatus and its method of use illustrated in the attached drawings, and described in the following specification are simply exemplary embodiments of the inventive concepts described herein. Specific dimensions and other physical characteristics relating to the embodiments disclosed herein are not to be considered as limiting unless expressly stated otherwise.

First Embodiment of the Apparatus

A first embodiment of the automated particulate extraction apparatus is shown at 40 in FIG. 2. This embodiment is comprised of a test tank 42 having a liquid cleaning medium dispensing system 44, which dispenses a liquid cleaning medium 46 into the test tank and onto one or more test parts 48. The liquid cleaning medium 46 is supplied from a dispensing source 50 such as a holding tank. The flow 51 of the liquid cleaning medium 46 is measured by an incoming liquid flow sensor 52 and is controlled via an inlet valve 54. In one form of the invention, the liquid cleaning medium dispensing system 44 is shaped into a ring shape 56 having a plurality of orifices 58 spaced around the diameter of the ring 56. This system ensures saturation of the test parts 48, but more importantly, also washes down the interior walls 60 of the test tank 42.

The test tank 42 is large enough to fit one or more test parts 48 into the tank, and in one preferred form of the invention contains a scrubbing element 62 which provide additional cleaning above that of the liquid cleaning medium dispensing system 44 itself. Preferred forms of the scrubbing element 62 include, but are not limited to cleaning jets 63, ultrasonic transducers 67, or an agitation source 69 to ensure that the liquid cleaning medium 46 contacts and interacts with the surfaces of the test parts 48. Further, one preferred form of the liquid cleaning medium 46 is Safety Kleen™ brand solvent, although other suitable solvents compatible with the test part 48 and the apparatus 40 may be selected. Alternate preferred solvents for the liquid cleaning medium 46 include mineral spirits, however any liquid medium could be used.

The test tank 42 further includes a lid 64 with a seal 66 which is preferably an O-ring sized to seal against the interior wall 60 of an opening 73 in the top 71 of test tank 42 in order to contain the liquid cleaning medium 46 within the test tank 42 when the tank is in operation. The test tank 42 also includes a depth sensor 68 which measures the depth of the liquid cleaning medium 46 within the test tank 42. This depth sensor 68, may be used in conjunction with the flow sensor 52 to determine the number of test parts in the tank if a per part volumetric displacement 47 is known.

To confirm the correct number of parts are in the test tank, the tank is filled to a set depth 49, wherein a corresponding volume of liquid cleaning medium is known, assuming the tank is empty or only has a parts basket or the like which is reused from test to test. This creates a known baseline volume 53. However, in an alternate measurement method, liquid cleaning medium 46 may be supplied and measured by the depth sensor 68 and stopped via an inlet valve 54 at a predetermined depth. The volume of the liquid cleaning medium 46 can then be measured with the incoming liquid flow sensor 52 and compared to a liquid displacement limit 120 to determine if a correct number of parts is supplied.

The bottom 70 of the test tank 42 is fitted with an outlet valve 72 which allows the liquid cleaning medium 46 to be removed from the test tank 42 and may be electrically actuated. Attached to the outlet valve 72 is a drain line 74 to which a liquid quality sensor 76 is installed. In a preferred form, the liquid quality sensor 76 is attached to the drain line 74 and is also preferably of the variety that allows for near real-time measurement of contaminants 78, such as non-dissolved solids 80 contained within the liquid cleaning medium 46 passing through the drain line 74. This liquid quality sensor may be mounted in any manner that allows for the sensor to measure the outflow of particulates contained in the liquid medium 46 after it leaves the test tank 42. While the most common placement for such as sensor, is 'in-line' with the drain line 74 sampling the entirety of the outflowing liquid, in-line placement is not required. The liquid quality sensor may be placed into a branch circuit, a separate liquid testing circuit, or even into a circuit parallel to the drain line, so long as it is capable of measuring the contamination level of the cleaning medium exiting the test tank.

Preferred forms of the liquid quality sensor 76 include, but are not limited to a turbidity sensor 82, which measures the cloudiness or haziness of a fluid caused by large numbers of individual contamination particles 78, or an instantaneous mass sensor 84 which measures the change in mass of the fluid. Fluid mass and cloudiness vary according to the level of contamination present in the liquid cleaning medium 46. Some examples of turbidity sensors 82 which may be used with the apparatus and method include both light based (optical or backscatter) 85 and magnetic based turbidity sensors 86. Some examples of instantaneous mass sensors 84 for use with the apparatus and method include mechanical, electronic, Coriolis 87 or Doppler 88 flow meters.

The aforementioned forms of liquid quality sensors 76 are merely exemplary, and not intended to be limiting. Any liquid quality sensor 76 which accurately detects the level of contaminants 78 within the liquid cleaning medium will support the methods provided herein. It is preferred however, that the sensors be able to repeatedly measure the liquid cleaning medium for changes in contamination levels during the machine's operation. Faster sample rates are preferred, as they allow for more data points to be entered into the quality array (database). Ideally, the preferred sensor should generate a near 'real-time' update to its data stream, voltage, or other output that may be used in the rapid calculation and determination of contamination levels in the system during operation.

As shown in FIG. 2, when the outlet valve 72 is opened, the liquid cleaning medium 46 passes from the test tank 42 and through the liquid quality sensor 76 wherein a measurement is made. The liquid cleaning medium 46 containing contaminants 78 from the test is then passed down a drain line 74 and into a liquid recovery vessel allowing for proper disposal. As shown in this figure, virgin liquid test medium is used in the process, and contaminated liquid test medium is passed into the recovery vessel, without reuse. This system setup ensures that the cleaning medium meets quality standards, and that any contaminants 78 measured by the liquid quality sensor 76 are derived from the test tank 42 or the test parts 48 themselves and not the liquid test medium.

Figure 3:
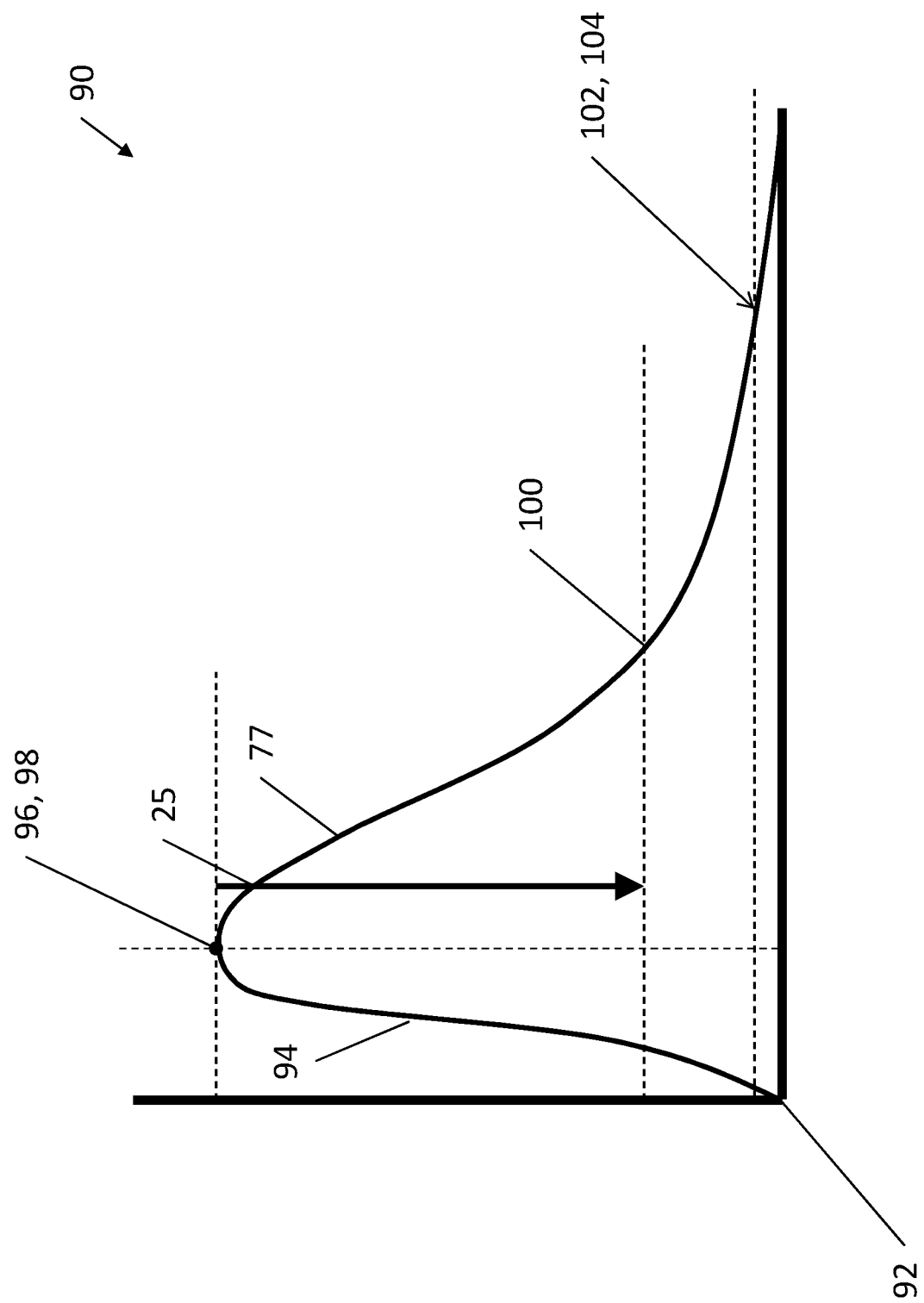
FIG. 3 is a graph showing cleaning medium contamination over time, as measured by an inline quality sensor.

The curve in FIG. 3 displays a graph showing liquid cleaning medium contamination 90 over time, as measured by the liquid quality sensor 76. Here, virgin liquid cleaning medium 46 is supplied to the test tank 42, and is used to clean the test part 48 via a combination of either or both of the dispensing system 44 and/or the scrubbing element 62. This removes contaminants 78 from the test part 48, some of which are non-dissolved solids which are then detected by the liquid quality sensor 76.

Method of Use for the First Embodiment of the Apparatus

As the process begins virgin fluid is placed into the test tank 42 and is also allowed to flow past the liquid quality sensor 76 wherein a baseline reading 92 is established. Test parts 48 are then cleaned in the test tank 42 increasing the level of contaminants 78 in the liquid cleaning medium 46. The measured values of contamination are then stored in a quality array 94 (a database storing data recording contamination levels versus time). As the cleaning process continues, the bulk of contamination on the test part 48 is washed off and into the liquid cleaning medium 46, thus the level of measured contaminants 78 (shown as the overall curve at 90) increases to a maximum point 96. This maximum or 'worst value' 98 as recorded by the liquid quality sensor 76 and is stored into the quality array 94, wherein the process continues until the values of contamination begin to fall off 77 below a part measurement threshold value 100. Once below the part measurement threshold, the test parts 48 are deemed sufficiently clean and could be removed from the system. However, instead of removing the parts, the cleaning process is preferably continued until such time as the measured contamination level 90 decreases below a second, lower contamination threshold called a tank clean threshold 102. The tank clean threshold 102 is the preferred stopping point because it ensures that the test tank 42 itself is sufficiently cleaned. Thus, the tank clean threshold 102 represents the end of the test 104. The lower contamination or tank clean threshold 102 may either be a fixed value, calculated as lying within a numerical percentage of desired tank cleaning 91 based on the either the baseline reading 92 as measured at the start of the test with clean fluid, or may be specified as a numerical cleaning cutoff value 97, which is calculated from the measured maximum value 98.

Figure 4:
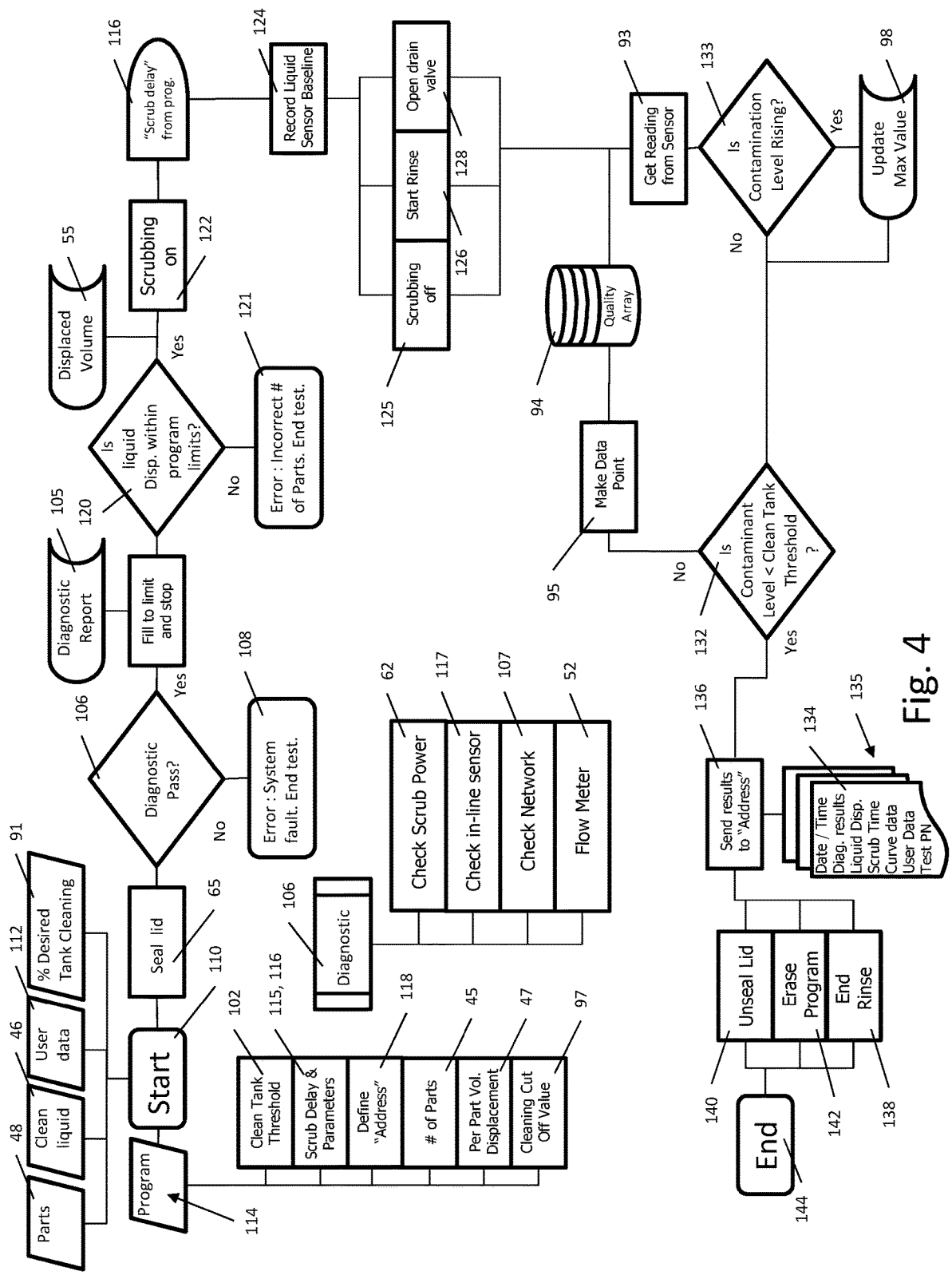
FIG. 4 is a flow chart describing a method of operation for the apparatus in its first form.

In FIG. 4, this process is expanded upon and includes several diagnostic checks 106 (generally) to ensure that the apparatus is operating properly. Starting at 110 in FIG. 4, a test part 48, virgin liquid cleaning medium 46, and user supplied data 112 (part identifying information, including but not limited to part number and lot number) are supplied to the apparatus 40 (generally), and specifically may be uploaded to a processing computer. A program 114 for the appropriate part number is then loaded into the apparatus 40. The program 114 includes definitions for a part measurement threshold value 100 which is either: a fixed value; calculated as a numerical cleaning cutoff value 97 as measured by the liquid quality sensor 76 from a 'worst value' (maximum value 98) measured during the process; or as defined to be within a certain percentage of a measurement made with clean fluid (baseline 92). The program 114 provides for an address 118, such as an IP (Internet Protocol) address, display device, storage device, or email address to which test results are to be sent at the conclusion of the process. The program 114 further includes scrub parameters 115 specifying how to operate the scrubbing element 62, and may include parameters which set a particular pressure, location, orientation, or motion for the scrubbing element 62. Further the scrub parameters 115 also preferably includes a scrub delay 116 which is a fixed time-based minimum cleaning time, or timer. This program may be run on a processor 113, such as a PLC, computer, micro logic controller, or the like having a storage memory 111 to hold variables and data. This processor is preferably connected to an external address 118 and the quality array 94.

At the start of the test 110, the program 114 is loaded into the apparatus, the test part 48 is loaded into the test tank 42 and the user data 112 pertaining to the test parts 48 are entered. The lid 64 is then sealed 65 onto the test tank 42 and a diagnostic test 106 is performed. The diagnostic test 106 comprises one or more of the following checks: 1) Verify scrubbing element 62 power is present; 2) Verify that the liquid quality sensor 76 is powered and within operational parameters; 3) Verify that network connections are present 107; 4) Verify that the incoming liquid flow sensor 52 into the tank is powered and within operational parameters (See. 117); 5) Verify that all valves (e.g. inlet valve 54 and outlet valve 72 are in the proper orientation (Closed/Closed).

If the diagnostic check fails 106, the system records the diagnostic error 108, and ends the test. If the diagnostic test 106 passes, an optional diagnostic report 105 is generated and the inlet valve 54 is opened allowing liquid cleaning medium 46 to flow into the tank. When a predetermined amount of liquid cleaning medium enters the tank according to the incoming liquid flow sensor 52 the inlet valve 54 is closed. An optional check to verify the correct count of test parts 48 is then conducted by verifying the liquid displacement is within limits 120 according to a depth sensor 68 when compared a calculation based on the user supplied data 112 and the difference in the fluid level of liquid cleaning medium within the tank when parts are added. If the liquid displacement is not within limits 120, a displacement error 121 is presented and the test ends. If the liquid displacement is within limits 120, the parts cleaning cycle begins 122 and the scrubbing element 62 is turned on and operated according to the scrub parameters 115, including the scrub delay 116. After the "scrub delay" 116 is reached, the liquid quality sensor 76 is zeroed (preferably with clean fluid creating a baseline reading 124), and the scrubbing element 62 is shut off 125. In an alternative form, the scrubbing element may be continued during the next step wherein the tank is rinsed and flushed. The rinse 126 and drain steps 128 are then conducted, wherein the outlet valve 72 is opened allowing liquid cleaning medium 46 containing contaminants 78 to pass the liquid quality sensor 76, which is preferably attached to the drain line 74. The level of contaminants 78 is monitored and the 'worst' or maximum value 98 (maximum measured contamination level as recorded from the liquid quality sensor) is recorded into a quality array 94. The rinse 126 operation continues to flow clean liquid cleaning medium 46 over the test parts 48 rinsing contaminants 78 from the test parts 48 and test tank 42 into the drain line 74 and past the liquid quality sensor 76.

The level of contaminants 78 is measured by the liquid quality sensor 76 and recorded into a quality array 94. Preferably this is done by storing individual values of the repeated measurements 93 into memory creating a datapoint 95, which are then written to the quality array 94. This data from the liquid quality sensor 76 is tracked by the apparatus's processor to confirm that the value of contamination first rises to a maximum and then begin to fall off 77 preventing a Type I error. Confirmation of the rise and fall of contaminants is shown in decision box 133 of FIGS. 4, 6 and 7.

The contamination is determined to have fallen off 77 when the present value of a contaminant reported from the sensor lies below the recorded maximum value 98 in the quality array. The rinse 126 process continues until the contamination level 78 reported by the liquid quality sensor 76 drops to a level lower than the part measurement threshold 100, to the tank clean threshold 102 as shown in decision box 132 in FIG. 4. This tank clean threshold 102 represents that the apparatus 40 is clean and ready to test another part. Results 134 of the test are stored in the quality array 94 are then transmitted 136 to the desired address 118. The rinse operation is then stopped 138, the lid unsealed 140, the program cleared 142 and the test complete 144. The apparatus 40 is now ready for another test and the test tank is clean and ready for reuse.

Second Embodiment of the Apparatus

Figure 5:
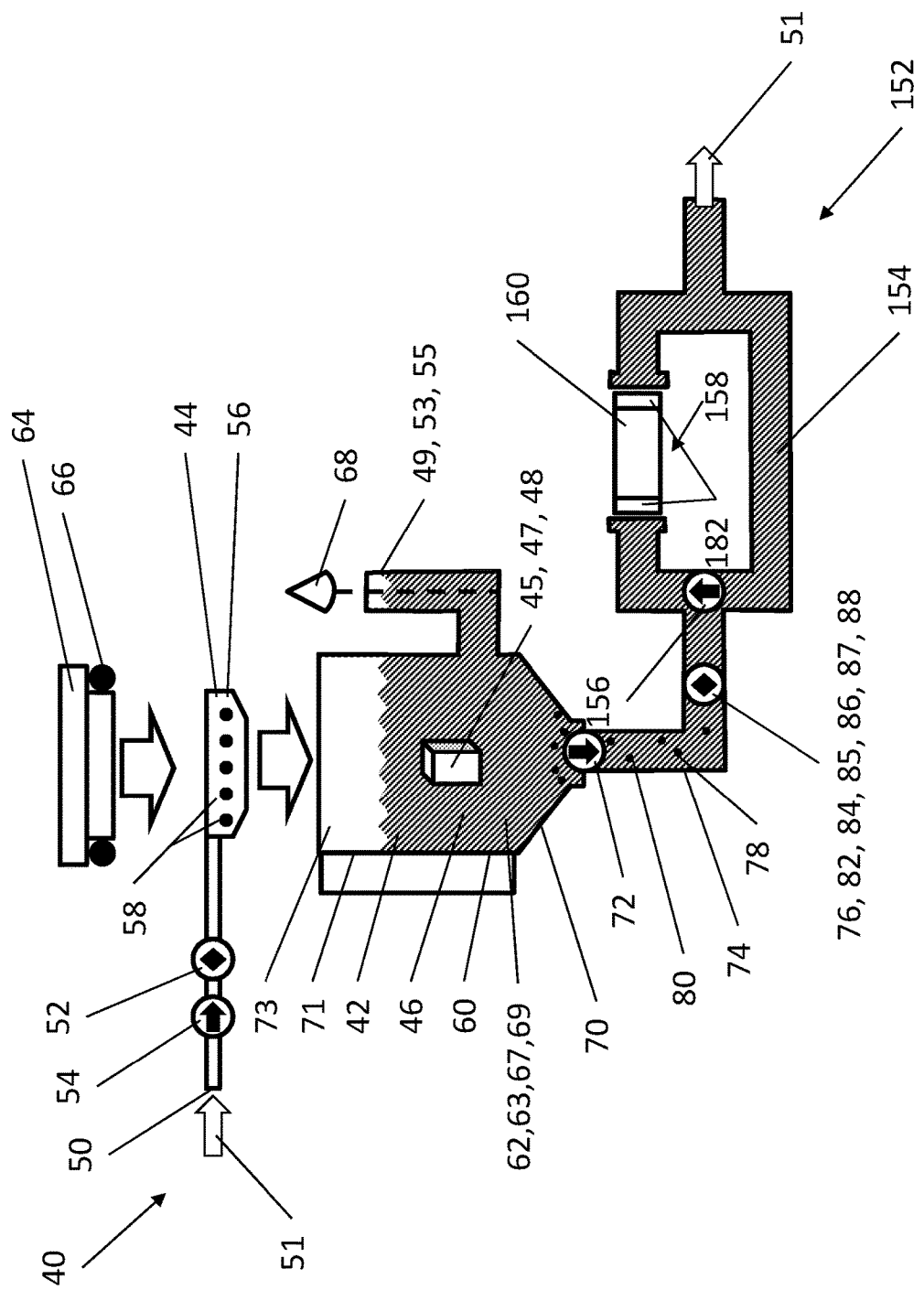
FIG. 5 is an elevation view of an apparatus according to a second form of the invention, this embodiment further comprising removable measurement filter medium.

A second embodiment of the invention is shown at 150 in FIG. 5, and builds upon the automated particulate extraction apparatus shown at 40 in FIG. 2, including the test tank 42, the scrubber element 62, the outlet valve 72, and the liquid quality sensor 76. However, the second embodiment of the apparatus 150 and method using this embodiment further comprises a testing station 152 and a bypass path 154 which are controlled by a bypass valve 156. The testing station 152 preferably includes a removable measurement filter 158 containing a filter medium 160. The bypass path 154, bypasses the testing station 152 when the bypass valve 156 is opened. This allows for the removable measurement filter 158 to be removed 159 for further analysis while the machine is still in operation. Alternate forms of this embodiment may include multiple removable filters 158 in series within the testing station 152, preferably wherein the separate filter medium 160 is selected at different pore sizes, e.g. 600 microns, and 10 microns. Further forms of the testing station 152 may include multiple removable filters in parallel to increase flow rate and reduce pressure loss.

Method of Use for the Second Embodiment of the Apparatus

Figure 6:
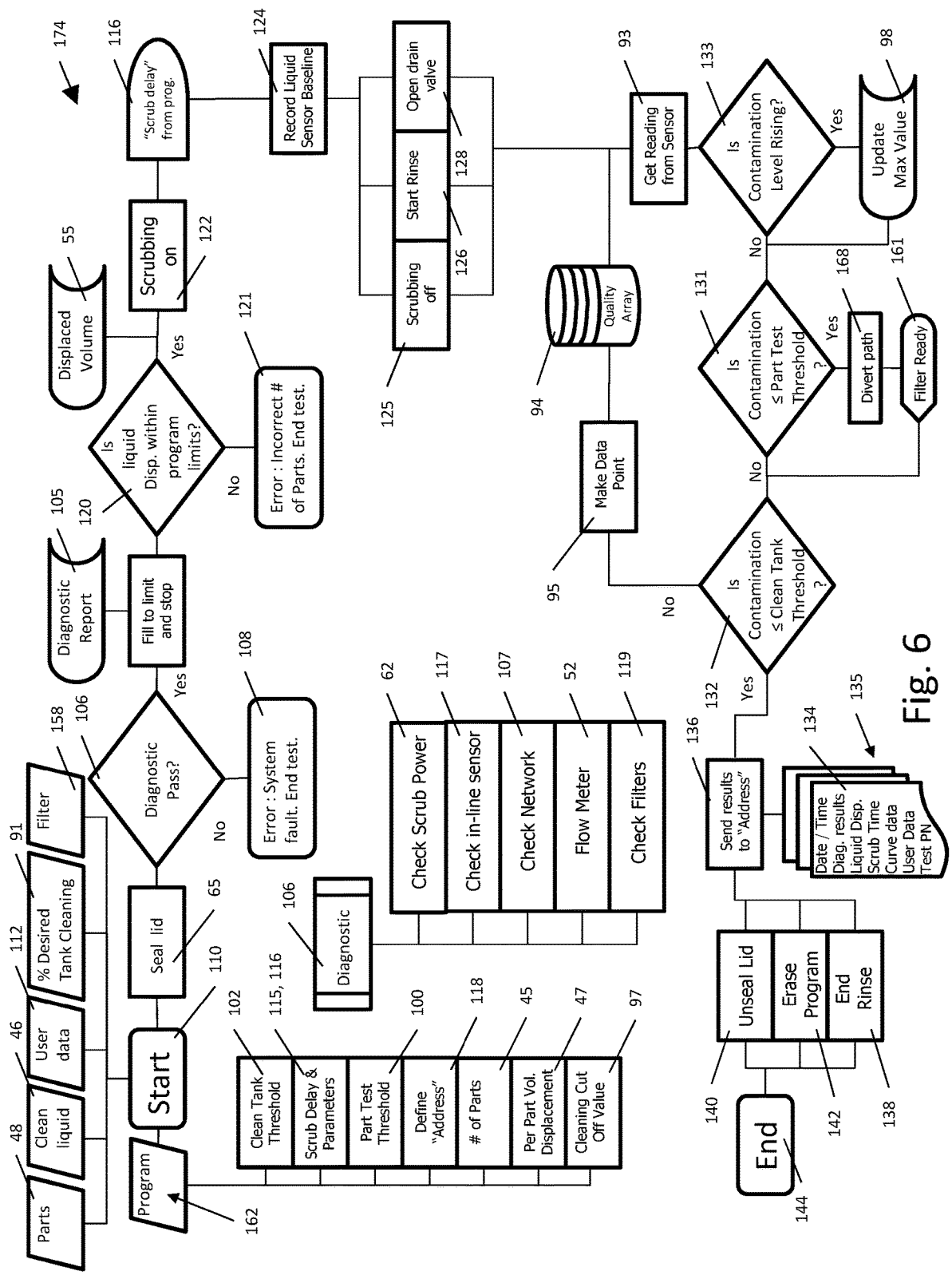
FIG. 6 is a flow chart describing a method of operation for the apparatus in its second form.
Figure 7:
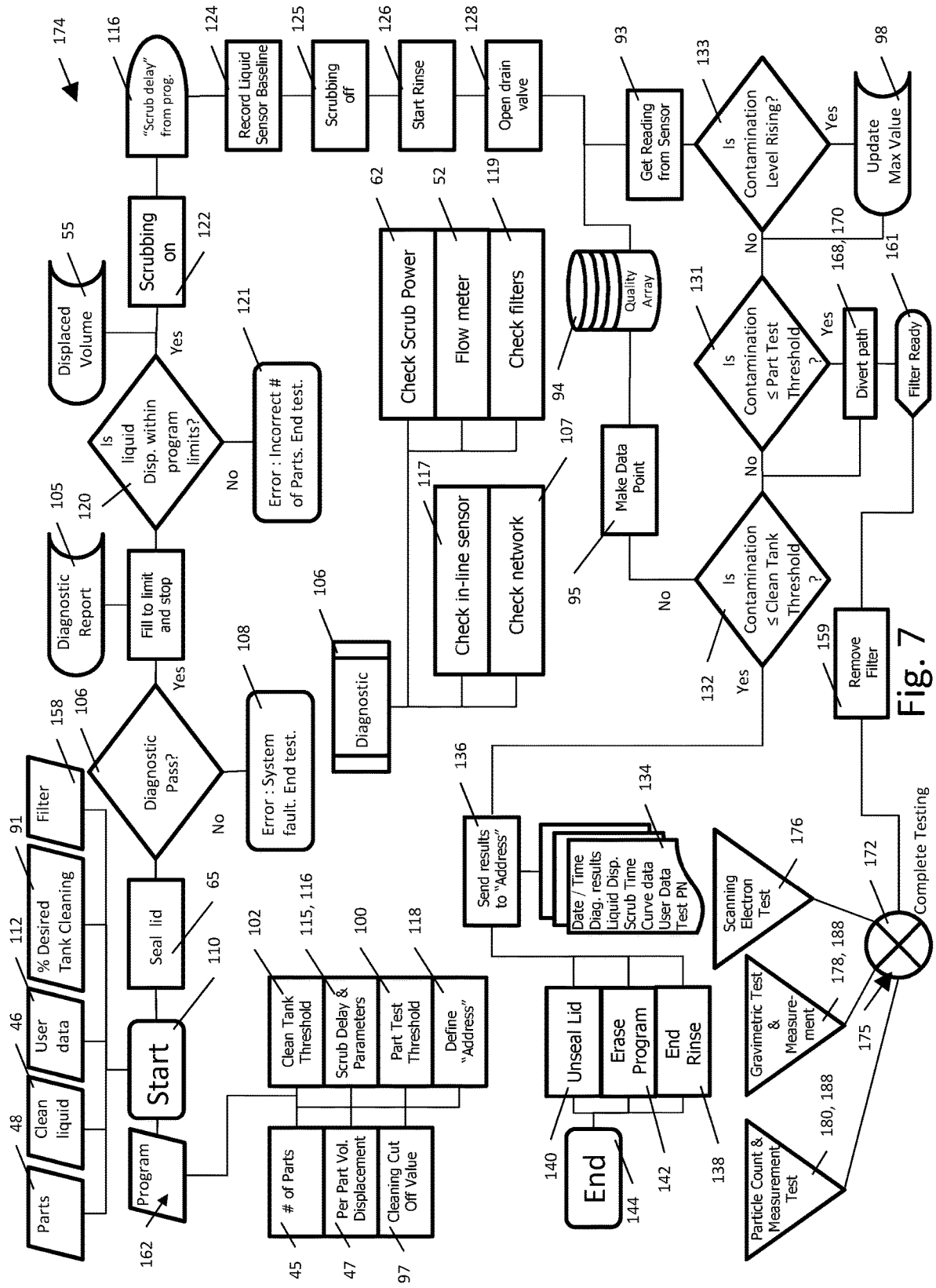
FIG. 7 is a flow chart describing a method of operation for the third embodiment of the apparatus including further testing of the filter medium.

The method of use of the second embodiment is shown at 162 in FIG. 6 and is similar to the method is shown at in FIG. 4, but adds the following additional steps. Diagnostic test 106 further includes verifying that the removable measurement filters 158 are in present and installed correctly (See 119). Next, the program 162 stored in the apparatus includes an additional variable called the part measurement threshold value 100 which represents the amount of cleaning proscribed for the test part 48 as a function of the maximum value 98 measured by the liquid quality sensor 76. One example of the numerical cleaning cutoff value 97 may be set to 60% of the worst measured value. This value would represent a goal of a 60% reduction in contaminant 78 values as calculated from the measured peak contaminant value for a test part 48 during a cleaning cycle. This part measurement threshold value is shown on the curve of FIG. 3. at 100. Either the part measurement threshold value 100 or the numerical cleaning cutoff value 97 may be loaded into the apparatus 150 as part of the program 114 and prior to the start of the process 162. The cleaning steps remain the same as in FIG. 4 wherein the test tank 42 is filled, the scrubbing element 62 is activated according to a set of scrub parameters 115, including a scrub delay 116 time period, after which the outlet valve 72 is opened allowing liquid cleaning medium 46 containing contaminants 78 into the drain line 74 wherein it flows past a liquid quality sensor 76. The contaminated fluid then passes through the testing station 152 and the removable measurement filter 158 trapping contaminants 78 in the filter medium 160.

As the liquid cleaning medium 46 containing contaminants 78 flows past the liquid quality sensor 76, measurement data is recorded into a quality array 94 wherein the "maximum value" 98 is continually updated and represents the peak contamination level measured by the liquid quality sensor 76. This peak value corresponds with maximum point 96 on the contamination curve 90 of FIG. 3. As the test tank 42 and test parts 48 are rinsed 126, the contamination level in the liquid cleaning medium 46 will begin to fall off. Testing for this rise and then fall avoids a Type I error, and is shown in decision box 133 in FIGS. 4, 6 and 7.

When the concentration of the contaminants 78 in the liquid cleaning medium 46 falls below the part measurement threshold 100, as measured by the liquid quality sensor 76, the bypass valve 156 is opened 168, and the flow 51 is diverted 170 into the bypass path 154. This bypass is shown in decision box 131 in FIGS. 6 and 7. This prevents additional contaminants 78 from reaching the removable measurement filters and their filter medium 160 after the part test measurement threshold 100 is reached. The removable measurement filters 158 may then be removed for further analysis, while the rinse step (cycle) 126 continues to operate. When the bypass valve is set to the bypass path 154, an optional filter ready indicator 161 may illuminate.

The rinse step 126 continues until the liquid cleaning medium 46 is measured to contain contaminants 78 below a tank clean threshold 102, similar to the decision box 132 of the method shown in FIG. 4. Once the contamination level in the liquid test medium 46 is below the tank clean threshold 102, the test tank 42 is deemed clean, the rinse process is stopped 138 and the quality array 94 of data 135 is transmitted 136 to the address 118. This data 135 may include, but is not limited to, the date, time, diagnostic results, the amount of liquid medium used, the contamination level as measured by the liquid quality sensor 76 and recorded during the test, the operator name, the part number, the lot number, etc. This test is completed 144 when the data 135 is sent 136 to the address 118 which may be to a computer, in the form of an email, or saved to a disk. The apparatus then unseals the lid 140, and optionally erases the program parameters 142 to ensure it is not reused with a different (incorrect) part number.

Method of Use for the Second Embodiment of the Apparatus with Additional Testing In addition to the method disclosed in FIG. 4, additional steps for processing the filter medium may be conducted in order to verify that the test part's 48 contamination levels are within specification using existing test standards (e.g. ISO-16232). In this alternate method 174 which is shown in FIG. 6, additional processing steps are shown at 172. These steps further processes the filter medium 160 to determine part contamination.

Comprehensive testing 175 includes one or more of the following steps performed on the filter medium 160 after it has completed a test cycle: 1) a scanning electron test 176, 2) a gravimetric test 178, and/or 3) a particle count test 180. For the scanning electron test 176, the filter medium 160 is dried, preferably in an oven, and the filter medium is then subjected to analysis under a scanning electron microscope wherein the surface of the filter medium is struck with a focused beam of electrons. The electrons then interact with contaminants 78 in the sample, producing various signals that contain information about the size and number of contaminants 78 which were extracted during the cleaning process. Since only a small portion of the filter medium 160 may be reviewed, the area subjected to the analysis will be considered representative for the rest of the sample. A set threshold based on size and quantity of contaminants then confirms if test part's contamination level exceeds the allowable threshold.

Concerning gravimetric testing 178, the filter medium 160 is massed before and after the cleaning process. The post-test filter medium is again dried to remove the liquid cleaning medium 46 and the weight of the filter medium 160 with contaminants 78 is compared to its initial value. The difference in mass, is thus directly related to the amount of contaminants 78 removed during the testing process 174. If multiple filter medium 160 are used each having a different porosity (preferably placed in series), then a mass may be correlated to a specific size of contaminant 78. For example, there may be a threshold of 0.05 mg of maximum contaminants for a 10 μm filter medium, and 0.01 mg maximum for a 150 μm filter medium. Placing multiple removable filters 158 in series 182 allows for such measurement 188.

Additionally, a particle count test 180 test may be performed. Here the filter medium 160 is again dried and then scanned by an automated microscope, wherein the individual contamination particles are identified, typed (e.g. Metallic, nonmetallic, fibers), measured, and categorized by size. Contaminants are assigned to size ranges, wherein each range has its own permissible maximum number of particles, e.g. 100 μm-200 μm having a maximum of 2,000 particles; and the 200 μm-650 μm range having a maximum of 16 particles. The location of each particle is held in memory until the end of the test so that larger particles may be further reviewed. Using reflectivity, slenderness ratios, and silhouettes, the individual contaminants are identified (Metallic, nonmetallic, fiber) and measured 188. The results are tabulated on a formal report which can be appended to the earlier electronic report transmitted 136 to the address 118.

Third Embodiment of the Apparatus

Figure 8:
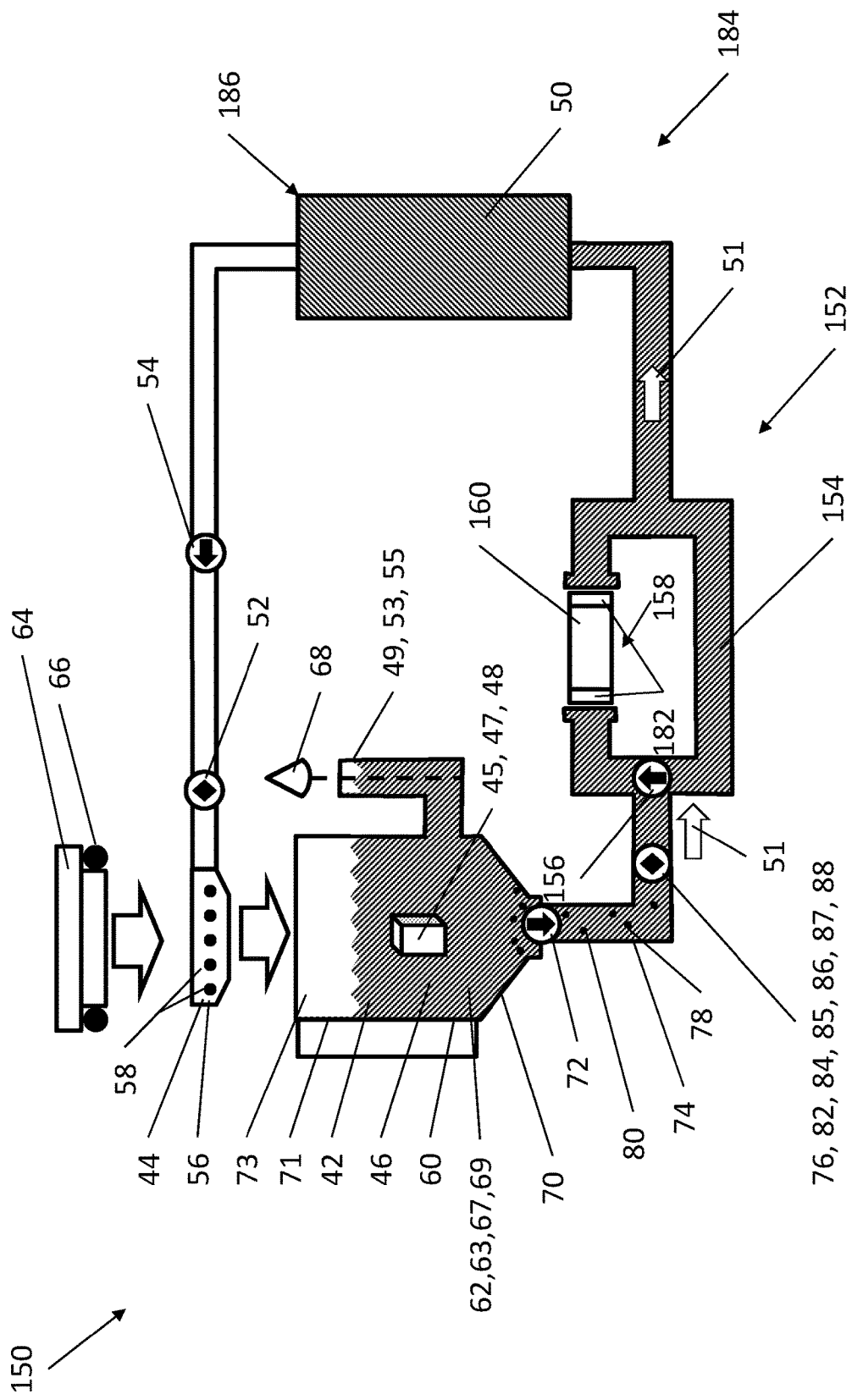
FIG. 8 is an elevation view of an apparatus according to a third form of the invention, this embodiment further comprising a system for purifying the liquid cleaning medium for reuse.

A third embodiment of the invention is shown in FIG. 8, and builds upon the automated particulate extraction apparatus shown at 150 in FIG. 5, including the test tank 42, the scrubber element 62, the outlet valve 72, the liquid quality sensor 76, the testing station 152 and a bypass path 154 which are controlled by a bypass valve 156. The testing station 152 again includes a removable measurement filter 158 containing a filter medium 160. However, in this embodiment, the apparatus is able to recycle and filter the liquid cleaning medium 46. This creates a closed loop system 184 (generally) minimizing hazardous waste, while ensuring that the liquid cleaning medium 46 is free from contaminants.

In one form of the third embodiment of the invention, the apparatus 150 is fitted with a liquid cleaning medium recycling system shown at 186 in FIG. 8. The recycling system 186 is fitted between the drain line 74 at the bottom 70 of the test tank 42 and the inlet line at the top of the tank 71 creating the closed loop 184. The recycling system 186 forms the dispensing source 50 supplying uncontaminated liquid cleaning medium 46 to the incoming liquid flow sensor 52 and inlet valve 54.

Several forms of the liquid cleaning medium recycling system 186 are compatible with the apparatus, but all must be able to remove contaminants 78 from the liquid cleaning medium 46 restoring it to acceptable levels of initial contamination. Preferably, the contamination level should be reduced as low as would be found in factory supplied liquid cleaning medium. Several methods of cleaning the liquid medium are acceptable for use with this apparatus and process. These include but are not limited to a bank of filters, an evaporative separator with solid waste removal, magnetic collection, centrifugal separation, and similar methods known in the art to separate contaminants from a liquid fluid.

The principle advantages offered by this invention include the ability to verify that a part has met the required cleanliness level as specified by a percentage reduction of contamination through the use of a liquid quality sensor 76 to measure the contamination of the part against the maximum value 98, which is the worst contamination level measured during a particular test. Once this reduction in contamination is achieved, the system is able to disconnect the measurement filter allowing a technician to process the results while the machine continues to clean itself. Further, the apparatus and method provided herein ensure that the test tank itself is sufficiently cleaned prior to the end of a test cycle by confirming that the apparatus is clean to within a specified threshold. This tank clean threshold may be specified as either a fixed value, or as defined to be within a certain percentage of a measurement made with clean fluid. This step ensures that residual contamination is removed from the test tank preventing a Type II, or false negative errors wherein residual contamination within the test chamber results in an otherwise acceptable part being rejected.

The above description is considered that of the preferred embodiments only. Modifications to the invention will occur to those skilled in the art and those who make use of the invention. Therefore, it is understood that the embodiments shown in the drawings and the examples set forth herein are described merely for illustrative purposes, and are not intended to limit the scope of the invention as interpreted according to the principles of patent law, including the doctrine of equivalents.

The invention claimed is:

1. A method for particulate extraction, comprising the steps of:
    providing a processor having a memory;
    providing a test tank having at least one wall and a bottom portion;
    providing a liquid cleaning medium dispensing system receiving a liquid cleaning medium;
    providing a drain line which allows the liquid cleaning medium to be removed from the test tank;
    providing a liquid quality sensing means;
    providing a part measurement threshold;
    providing a tank clean threshold;
    inserting a removable measurement filter downstream from the liquid quality sensing means;
    providing a bypass path around the removable measurement filter, said bypass path activated by a bypass valve;
    placing at least one solid test part into the test tank;
    cleaning the at least one solid test part and the test tank by allowing the liquid cleaning medium to contact both the at least one solid test part and the test tank, thereby creating a contaminated liquid cleaning medium, which is then allowed to exit the test tank;
    repeatedly measuring an amount of a contaminant present in the contaminated liquid cleaning medium using the liquid quality sensing means, thereby creating a contamination measurement value;
    continuing the step of cleaning until the contamination measurement value has both increased and then decreased;
    recording a maximum value of the contamination measurement value and storing it in the memory;
    passing the contaminated liquid cleaning medium through said removable measurement filter to capture the contaminant on said removable measurement filter;
    continuing the step of cleaning until the contamination measurement value falls below the part measurement threshold, wherein the bypass valve is activated, bypassing the removable measurement filter;
    continuing the step of cleaning while bypassing the removable measurement filter until the contamination measurement value falls below the tank clean threshold, wherein the step of cleaning is stopped;
    removing the at least one solid test part;
    removing the removable measurement filter; and
    measuring or counting the contaminant captured on the removable measurement filter.

2. The method as defined in claim 1, further comprising the steps of:
    providing a numerical cleaning cutoff value; and
    calculating the part measurement threshold by multiplying the numerical cleaning cutoff value by the maximum value.

3. The method as defined in claim 1, further comprising the steps of:
    sending the liquid cleaning medium past the liquid quality sensing means and measuring a baseline reading prior to the step of cleaning; and
    recording the baseline reading in the memory.

4. The method as defined in claim 1, further including the steps of:
    providing an inlet valve controlling the liquid cleaning medium entering into the liquid cleaning medium dispensing system;
    providing an outlet valve controlling the contaminated liquid cleaning medium exiting the test tank; and
    filling the test tank with the liquid cleaning medium immersing the at least one solid test part.

5. The method as defined in claim 1, further including the steps of:
    providing a scrubbing means; and
    scrubbing the at least one solid test part with the scrubbing means.

6. The method as defined in claim 1, further including the steps of:
    providing a scrubbing means;
    filling the test tank with the liquid cleaning medium immersing the at least one solid test part; and
    scrubbing the at least one solid test part with the scrubbing means after the step of filling the test tank.

7. The method as defined in claim 4, further comprising the steps of:
    providing a per-part volumetric displacement value;
    providing a user provided number of parts;
    supplying a measured volume of the liquid cleaning medium to the test tank sufficient to immerse the at least one solid test part;
    measuring a depth of the liquid cleaning medium;
    calculating a displaced volume using the depth and storing it into the memory of the processor;
    determining an actual part count by calculating a difference between the displaced volume and the measured volume and dividing the difference by the per-part volumetric displacement value; and
    comparing the actual part count against the user provided number of parts.

8. The method as defined in claim 5, further comprising the steps of:
    providing a scrub parameter;
    operating the scrubbing means according to the scrub parameter; and afterwards
    erasing the scrub parameter from the memory.

9. The method as defined in claim 3, further comprising the steps of:
    storing a numerical percentage of desired tank cleaning in the memory; and
    calculating the tank clean threshold by multiplying the numerical percentage of desired tank cleaning by the baseline reading.

10. The method as defined in claim 1, further comprising the steps of:
    storing a numerical percentage of desired tank cleaning in the memory; and
    calculating the tank clean threshold by multiplying the numerical percentage of desired tank cleaning by the maximum value.

11. A method for particulate extraction, comprising the steps of:
    providing a test tank having at least one wall and a bottom portion;
    providing a liquid cleaning medium dispensing system receiving a liquid cleaning medium;

providing an inlet valve controlling the liquid cleaning medium entering into the liquid cleaning medium dispensing system;
providing a drain line which allows the liquid cleaning medium to be removed from the test tank;
providing an outlet valve;
providing a processor having a memory;
providing a liquid quality sensing means;
providing a scrub parameter;
storing the scrub parameter into the memory;
providing a numerical percentage of desired tank cleaning;
storing the numerical percentage of desired tank cleaning into the memory;
providing a scrubbing means;
providing a removable measurement filter downstream from the liquid quality sensing means;
providing a bypass path around the removable measurement filter, said bypass path activated by a bypass valve;
placing at least one solid test part into the test tank;
sending the liquid cleaning medium past the liquid quality sensing means and measuring a baseline reading;
storing the baseline reading into the memory;
scrubbing the at least one solid test part by operating the scrubbing means according to the scrub parameter;
cleaning the at least one solid test part and the test tank by allowing the liquid cleaning medium to contact the at least one solid test part and the test tank, thereby creating a contaminated liquid cleaning medium;
allowing the contaminated liquid cleaning medium to exit the test tank;
controlling the contaminated liquid cleaning medium exiting the test tank by operating the outlet valve;
repeatedly measuring an amount of a contaminant present in the contaminated liquid cleaning medium using the liquid quality sensing means, thereby creating a contamination measurement value;
comparing the contamination measurement value to a previous value and determining if the contamination measurement value has increased or decreased;
continuing the step of cleaning until the contamination measurement value has both increased and then decreased;
recording a maximum value of the contamination measurement value into the memory;
calculating a tank clean threshold by multiplying the numerical percentage of desired tank cleaning by the baseline reading; storing the tank clean threshold into the memory;
providing a numerical cleaning cutoff value;
storing the numerical cleaning cutoff value into the memory;
calculating a part measurement threshold by multiplying the maximum value by the numerical cleaning cutoff value;
storing the part measurement threshold into the memory;
capturing the contaminant present in the contaminated liquid cleaning medium in the removable measurement filter;
activating the bypass valve when the contamination measurement value falls below the part measurement threshold thereby bypassing the removable measurement filter;
removing the removable measurement filter;
continuing the step of cleaning without using the removable measurement filter until the contamination measurement value falls below the tank clean threshold, wherein the step of cleaning is stopped; and
removing the at least one solid test part from the test tank.

12. The method as defined in claim 11, further including the steps of:
providing a liquid displacement limit;
measuring a depth of the liquid cleaning medium present in the test tank; and
filling the test tank with the liquid cleaning medium to the liquid displacement limit prior to operating the scrubbing means.

13. The method as defined in claim 11, further including the step of measuring or counting the contaminant captured on the removable measurement filter.

14. The method as defined in claim 11, further including the step of repeatedly storing an individual value of contamination measurement value into the memory creating a datapoint; and storing the datapoint to a quality array.

15. The method as defined in claim 14, further including the step of transmitting the quality array to an address.

16. The method as defined in claim 14, further including the step of:
erasing the datapoint; and
erasing at least one of the following from the memory: the scrub parameter; the numerical cleaning cutoff value; the baseline reading; or the numerical percentage of desired tank cleaning.

17. The method as defined in claim 11, further including the steps of:
providing a per-part volumetric displacement;
storing the per-part volumetric displacement into the memory;
measuring a volume of the liquid cleaning medium entering the test tank;
filling the test tank to a known depth, said known depth having a known baseline volume;
storing the volume of the liquid cleaning medium entering the test tank into the memory;
calculating a total part volume displacement within the test tank by subtracting the measurement of the volume of the liquid cleaning medium entering the test tank from the known baseline volume;
calculating a part count by dividing the total part volume displacement within the test tank by the per-part volumetric displacement; and
storing the part count into the memory.

18. The method as defined in claim 11, further including the steps of:
providing a lid having a liquid tight seal; and
using the lid to seal an opening located on a top portion of the test tank.

19. A method for particulate extraction, comprising the steps of:
providing a test tank having at least one wall, and a bottom portion;
providing a liquid cleaning medium dispensing system receiving a liquid cleaning medium;
providing an inlet valve controlling the liquid cleaning medium entering into the liquid cleaning medium dispensing system;
providing a drain line which allows the liquid cleaning medium to be removed from the test tank;
providing an outlet valve;
providing a liquid quality sensing means;
providing a scrubbing means;
inserting a removable measurement filter downstream from the liquid quality sensing means;

providing a bypass path around the removable measurement filter, said bypass path activated by a bypass valve;

providing a processor having a memory;

storing a scrub parameter into the memory of the processor;

storing a numerical cleaning cutoff value into the memory of the processor;

providing a per-part volumetric displacement value;

providing a user provided number of parts;

providing a tank clean threshold;

placing at least one solid test part into the test tank;

supplying a measured volume of the liquid cleaning medium entering the test tank sufficient to immerse the at least one solid test part;

measuring a depth of the liquid cleaning medium;

calculating a displaced volume using the depth and storing it into the memory of the processor;

determining an actual part count by calculating a difference between the displaced volume and the measured volume and dividing the difference by the per-part volumetric displacement value;

scrubbing the at least one solid test part with the scrubbing means according to the scrub parameter;

cleaning the at least one solid test part and the test tank by allowing the liquid cleaning medium to contact both the at least one solid test part and the test tank, thereby creating a contaminated liquid cleaning medium, which is then allowed to exit the test tank;

repeatedly measuring an amount of a contaminant present in the contaminated liquid cleaning medium using the liquid quality sensing means, thereby creating a contamination measurement value;

continuing the step of cleaning until the contamination measurement value has both increased and then decreased;

recording a maximum value of the contamination measurement value;

calculating a part measurement threshold by multiplying the numerical cleaning cutoff value by the maximum value;

passing the contaminated liquid cleaning medium through said removable measurement filter to capture the contaminant on said removable measurement filter;

continuing the step of cleaning until the contamination measurement value falls below the part measurement threshold, wherein the bypass valve is activated, bypassing the removable measurement filter;

continuing the step of cleaning while bypassing the removable measurement filter until the contamination measurement value falls below the tank clean threshold, wherein the step of cleaning is stopped;

removing the at least one solid test part;

removing the removable measurement filter; and measuring or counting the contaminant captured on the removable measurement filter.

20. The method as defined in claim 1, further comprising the step of: drying the removable measurement filter thereby preserving the contaminant captured on said removable measurement filter.

21. The method as defined in claim 1, further comprising the step of:

passing the contaminated liquid cleaning medium through a liquid cleaning medium recycling means wherein the liquid cleaning medium is recycled and returned to the liquid cleaning medium dispensing system.

22. The method as defined in claim 1, further comprising the step of:

passing the contaminated liquid cleaning medium through an evaporative separator wherein the liquid cleaning medium is recycled and returned to the liquid cleaning medium dispensing system.

23. The method as defined in claim 11, further comprising the steps of:

erasing the part measurement threshold from the memory of the processor; and erasing the tank clean threshold from the memory of the processor.

24. The method as defined in claim 1, further comprising the step of:

providing at least two removable measurement filters having different pore sizes.

\* \* \* \* \*